United States Patent [19]

Flagg

[11] 4,435,381

[45] Mar. 6, 1984

[54] THIOURONIUM PHOSPHONATES FOR USE IN DENTAL TREATMENTS

[75] Inventor: Edward E. Flagg, Midland, Mich.

[73] Assignee: The Dow Chemical Company, Midland, Mich.

[21] Appl. No.: 514,999

[22] Filed: Jul. 18, 1983

[51] Int. Cl.³ .......................... A61K 7/16; A61K 7/22
[52] U.S. Cl. ........................................ 424/54; 424/199
[58] Field of Search ................................ 424/49–58, 424/199; 260/501.21

[56] References Cited

U.S. PATENT DOCUMENTS

| | | | |
|---|---|---|---|
| 2,605,278 | 7/1952 | Mikeska | 260/461 |
| 2,774,706 | 12/1956 | Hackmann et al. | 167/22 |
| 2,980,578 | 4/1961 | Abramitis | 167/22 |
| 3,891,704 | 6/1975 | Diamond | 260/564 E |

OTHER PUBLICATIONS

Chem. Abstr. 85: 186592C (1976).

*Primary Examiner*—Shep K. Rose
*Attorney, Agent, or Firm*—Edward P. Gray; Ronald G. Brookens

[57] ABSTRACT

Process and composition for dental hygiene in which the teeth of animals are contacted with a long-chain alkyl thiouronium phosphonate.

9 Claims, No Drawings

THIOURONIUM PHOSPHONATES FOR USE IN DENTAL TREATMENTS

BACKGROUND OF THE INVENTION

This invention is directed to a process for the prevention of dental caries and periodontal disease in animals which comprises contacting the dental surfaces with an effective amount of a thiouronium phosphonate chemotherapeutic agent. Advantageously, an appropriate pharmaceutically acceptable carrier such as a toothpaste, tooth powder or mouthwash can be used as the phosphonate vehicle.

Dental disease in animals is one of the most pervasive, non-life threatening medical problems encountered by man, affecting nearly all individuals at some time during their lives. The two most common dental pathologies are dental caries and periodontal disease. There are differing opinions as to the etiology of these diseases, but in all theories there is one common denominator—the presence of an acid-producing, acid-tolerating microorganism.

The dental decay process starts with the demineralization of the tooth enamel. The utilization of dietary carbohydrates by the bacteria in the synthesis of ATP produces an acidic metabolic waste product which, when contacted with dental enamel, initiates decay. This is followed by a progressive loss of tooth enamel.

Presumably, the normal dynamics of the oral cavity such as chewing, swallowing, the movement of the tongue or the flow of saliva would inhibit the accumulation of acid on the dental surfaces. However, because of the synthesis of dental plaque, the bacteria and their acidic waste products are held in contact with the tooth surfaces for a time sufficient to begin the demineralization process of the enamel.

Plaque is thought to be a soft, organic matrix consisting of a mixture of salivary glyco-protein and bacterial extracellular polysaccharides. It is within this sticky mass that bacteria become embedded. The matrix rapidly thickens on the surfaces of the teeth after eating and becomes an adhesive film which cannot be removed by the dynamics of the oral cavity or be washed off with water. Plaque, then, plays a significant role in the etiology of dental caries as it effectively serves to bind the bacteria to the dental surfaces and buffers the effects of saliva and other self-cleaning mechanisms of the mouth.

Several genera of oral bacteria have been isolated and are known to be cariogenic. The filamentous organisms of the Actinomyces genus, Nocardia, various strains of lactobacilli, and the streptococci have all been implicated in the decay process. Of the genera mentioned, the largest group involved in dental decay are the streptococci. Representative organisms which inhabit the oral cavity include *S. mitis, S. mutans, S. salivarius,* and *S. sangius.* The most important of these in terms of odontopathic effect is *S. mutans.* The ability of *S. mutans* to produce dental disease in man is well documented. It has been found that animals which tend to have a higher incidence of dental caries also have a greater concentration of *S. mutans* in the oral cavity.

The greater cariogenicity of *S. mutans* seems to be related to two factors which are of critical importance in the decay process. First, *S. mutans* has been termed a primary plaque former. The organism has the capability of producing greater quantities of extracellular polysaccharides, one of the components of the plaque matrix. Secondly, *S. mutans* has the capacity to produce greater quantities of acid than other streptococci which inhabit the oral cavity. These two metabolic processes are carried on simultaneously and the effects are significant. For example, when sucrose is metabolized by *S. mutans,* it is broken down into its component sugars, glucose and fructose. The glucose forms the dextran chain of the polysaccharide portion of plaque, while the fructose is further metabolized to lactic acid which is then held in close proximity to the dental surface to initiate or propagate the decay process.

Plaque has also been shown to be important in the etiology of the periodontal disease process. Periodontal disease affects the tissues surrounding and supporting the teeth, such as the periodontal membrane, the cementum, the alveolar bone and the gingiva. As these tissues weaken, the teeth gradually loosen and ultimately become unable to function in mastication.

The role of plaque in the periodontal disease process is similar to that in dental caries. It provides an adhesive covering over the periodontium whereby the bacteria are brought into contact with the soft connective tissue. It also acts as a buffer to the normal self-cleaning mechanisms of the oral cavity and provides an anaerobic environment which is essential to the survival of the microorganisms.

Generally, bacteria cited as being cariogenic have also been implicated in the periodontal disease process. Most notably is the deleterious effect of *S. mutans* on alveolar bone. Sharawy and Socransky discovered a significantly greater alveolar bone loss in laboratory mice and rats exposed to *S. mutans* as compared to non-exposed control groups (46 *Journal of Dental Research,* 1385, 1967). Other bacteria known to be involved in the periodontal disease process include *Streptococcus salivarius, Actinomyces naeslundii,* and various strains of *Rothia, Neisseria,* and *Bacterionema.*

Historically, the control of the dental disease process has focused on three separate areas: diet modification, host resistance, and bacteria-directed control. The diet modification approach has met with little success. It comprises eliminating from food sweeteners such as sucrose or the substitution of a non-hydrolyzable sugar such as xylitol. The elimination of sucrose from the diet involves changing eating and cooking habits which most people are not ready to make. The use of xylitol is feasible, but may be prohibitively expensive.

Attempts directed at increased host resistance to dental disease have received the most attention over the years. Procedures such as enzyme inhibition of plaque formation, resin-based plastic sealants over the articulating surfaces of the molars, and vaccine immunizations have met with little or no success. Topical fluoride applications to the teeth as well as dietary supplements of fluoride have been successful in strengthening the hydroxyapatite crystal lattice structure of enamel with a concomitant decrease in the rate of tooth decay.

Methods of disease control directed to the microbial flora in the mouth is the latest area to receive consideration. Since the role of microorganisms in the disease process is now known, attempts at control through the use of chemotherapeutic agents is desirable. Antibiotics such as penicillin, erythromycin, vancomycin and spiramycin have been shown to control the dental disease process either through a cidal effect on the causative organism or through a plaque-inhibiting process. However, the widespread use of these antibiotics could lead to resistant strains of microorganisms, potentially rendering the antibiotics useless in life-threatening situations. Because of this, it is felt that the widespread use of antibiotics in dental prophylaxis is not feasible.

Consequently, it would be desirable to utilize an anti-microbial which has a sufficiently broad spectrum to eliminate from the oral cavity organisms known to be cariogenic or that cause dental pathologies. Similarly, it would be desirable that this anti-microbial and compositions containing it be effective in low doses, and not cause staining of the teeth and oral mucosa, nor should it cause other oral irritation.

SUMMARY OF THE INVENTION

It has now been discovered that thiouronium phosphonate compounds of the formula

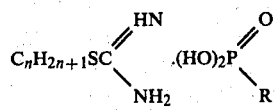

(known in the ionic form $C_nH_{2n+1}SC(NH_2)_2{}^+HO(O^-)PR$), are useful in preventing dental caries and periodontal disease by contacting dental surfaces with an effective amount of from about 0.1% to about 0.5% of one or more such thiouronium phosphonate compounds. Advantageously, a pharmaceutically acceptable carrier such as a toothpaste, tooth powder or mouthwash is used as a vehicle. In the above formula, R represents hydrogen, methyl or phenyl, of which phenyl is preferred, and n represents an integer of from about 10 to about 14, of which 12 is preferred.

The compounds used in this invention are preferred to analogous thiouronium bromides and chlorides (which have been used as plant fungicides), because of their greater thermal and hydrolytic stability and absence of offensive odors. These properties are advantageous for dental hygiene applications in the oral cavity because of concomitant properties, i.e., greater shelf life, more reliable formulations and lack of rejection by potential recipients. Hamsters, for example, have been observed to reject dosages of thiouronium bromide or chloride in Methocel ® solutions. No examples of animal rejection (hamster or rats) were observed for the phosphonates utilized herein. It is believed that a direct correlation exists between stabiity and odor, i.e., the malodorous properties of analogous thiouronium bromides and chlorides result from small amounts of decomposition products, primarily thiols.

Preparation of Thiouronium Phosphonates

The following schematic equations will help in understanding the preparation of the thiouronium phosphonates used in practicing the invention. The starting material is a thiouronium hydrochloride or hydrobromide which may be prepared by known methods (e.g., U.S. Pat. No. 2,980,578, patented Apr. 18, 1961):

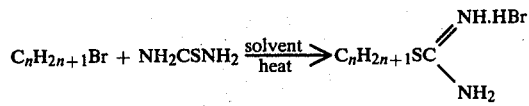

The thiouronium bromide (chloride may be used) is then transformed to a phosphonate salt by an anion exchange process, to give the compounds herein utilized:

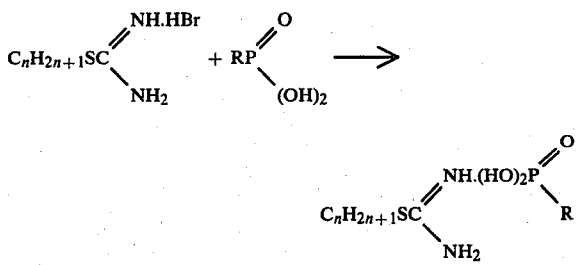

In the above schematic equations, n and R have the significance previously given. A procedure for such anion exchange is shown in U.S. Pat. No. 2,605,278, patented July 29, 1952, wherein the anion is derived from heptadecylphenyl-hydroxy methyl phosphonic acid.

The following examples are merely illustrative of the thiouronium phosphonates as generically described and specifically exemplified and are not to be construed as a limitation thereon.

EXAMPLE 1 n-Decyl thiouronium phenylphosphonate 11.7 Grams (g) of n-Decyl thiouronium bromide, 14.0 g of phenylphosphonic acid, and 300 milliliters (ml) of ethanol were heated near 80° C. for approximately 16 hours. The solution was concentrated by solvent evaporation and a precipitate formed when water (about 50 ml) was added. After cooling overnight and filtering, the solid which was isolated was redissolved in 300 ml of ethanol and 100 ml of water by heating. The hot solution was filtered and a colorless precipitate formed upon cooling. Elemental analysis and infrared spectra confirmed the formation of n-decyl thiouronium phenylphosphonate, melting point (m.p.) 154°-157° C.

EXAMPLE 2 n-Tetradecyl thiouronium methanephosphonate n-Tetradecyl thiouronium bromide (10.2 g) was dissolved in water (200 ml) by heating and an ethanol solution (75 ml) of methanephosphonic acid (5.8 g) was added. The mixture was concentrated and a solid was isolated upon cooling. This solid was dissolved in a hotwater-ethanol mixture, filtered, then cooled concurrently with partial solvent evaporation. The recrystallization was repeated using an additional 3 g of methanephosphonic acid and 50 ml of ethanol. A colorless solid with a m.p. of 151°-152.5° C. was isolated. Chemical analysis and infrared spectra confirmed the formation of n-tetradecyl thiouronium methanephosphonate.

EXAMPLE 3 n-Dodecyl thiouronium phenylphosphonate n-Dodecyl thiouronium chloride (8.0 g), phenylphosphonic acid (10 g), and 200 ml of 50/50 (v/v) ethanol/water mixture were heated overnight and then cooled. After filtering and recrystallizing from water-methanol-ethanol, approximately 11.1 g of n-dodecyl thiouronium phenyl phosphonate was isolated (m.p. 154°-156° C.). Chemical analysis and infrared spectra confirmed n-dodecyl thiouronium phenylphosphonate formation.

EXAMPLE 4 n-Dodecyl thiouronium hydrogenphosphonate n-Dodecyl thiouronium bromide (about 0.0495 mole) and hydrogen phosphonic acid (about 0.15 mole) were mixed and heated at about 90° C. to remove HBr. Water was added and the mixture was filtered (a nitrogen stream was used to remove oxygen). Approximately 12.4 g of the desired n-dodecyl thiouronium hydrogen phosphonate was isolated, m.p. 119°–122° C. The compound was re-precipitated from ethanol and water. The IR data were consistent with $HPO^-_3$ as the counterion, i.e., strong bands near 1195 $cm^{-1}$, 1145 $cm^{-1}$, 1097 $cm^{-1}$, 991 $cm^{-1}$ and 927 $cm^{-1}$. A sharp band was also observed at 2380 $cm^{-1}$ which is characteristic of the P-H linkage.

The compounds used herein were identified as follows:

Infrared bands of the thiouronium phosphonates near 1020, 1120, and 1170 were moderately strong and characteristic of spectra with phosphonate moieties. These bands were absent for the corresponding bromides and chlorides.

Elemental analyses:

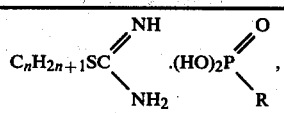

| | | Found (Calculated) | | | |
|---|---|---|---|---|---|
| n | R | C | H | N | m.p., °C. |
| 10 | C6H5 | 54.6(54.5) | 8.22(8.34) | 7.45(7.48) | 154–157 |
| 11 | C6H5 | 55.7(55.6) | 8.65(8.56) | 7.14(7.21) | 154–155.5 |
| 12 | H | 48.0(47.8) | 9.50(9.57) | 8.14(8.58) | 119–122 |
| 12 | C6H5 | 56.9(56.7) | 8.81(8.76) | 6.88(6.96) | 154–156 |
| 13 | C6H5 | 57.8(57.7) | 8.89(8.95) | 6.73(6.73) | 150–151 |
| 14 | CH3 | 52.2(52.1) | 10.27(10.1) | 7.70(7.60) | 151–152.5 |

Table 1 shows the minimum inhibitory concentrations (MIC) and minimum bactericidal concentrations (MBC) in parts per million against *S. mutans* grown in a typical culture medium. Acid inhibition (AI) is a measure of acid production when *S. mutans* attacks sucrose to form pyruvic and lactic acids. The organism is added to a culture medium (trypticase-yeast) containing sucrose, and after 48 hours incubation, the quantity of 0.1 normal NaOH (in ml) needed to neutralize the acid is measured. The amount (in ml) of 0.1 normal NaOH required is the AI value which is also shown in Table 1.

TABLE 1

| n | R | MIC | MBC | AI |
|---|---|---|---|---|
| 10 | C6H5 | 2 | 3.9 | 1.25 |
| 11 | C6H5 | 1 | 2 | 0.5 |
| 12 | C6H5 | 1 | 1 | 0.25 |
| 13 | C6H5 | 1 | 2 | 0.3 |
| 14 | CH3 | 1 | 7.8 | 0.5 |

Representative thiouronium phosphonates were tested against hamsters as in vivo subjects, as follows.

Golden Syrian hamsters (3–4 wks of age), obtained from GIBCO Animal Resources Laboratories, Madison, Wis. were used in all studies. Upon receipt, the animals were randomly distributed into cages of three animals of the same sex per cage. Experimental groups consisted of twelve animals, six males and six females. Food (Diet 2000, General Biochemicals Co.) and deionized water were allowed ad libitum. Food consumption was monitored three times a week while animal weights were checked twice a week.

After an acclimation period of 10 days, the oral cavities of the hamsters were infected with a cariogenic strain of *S. mutans* (ATCC 10449, SR 500). This was accomplished by injecting 100 ml of a 24 hr. culture grown static in Todd-Hewitt broth (supplemented with 0.5% lactalbumin hydrolysate) into their mouths, and by adding 2 ml/100 ml of the culture to their drinking water. This was repeated daily for four days. On the fifth day, fresh water was given to the hamsters.

To insure that the organism had actually implanted, the oral cavity of each hamster was swabbed on the sixth day. The swabs were then incubated in Todd-Hewitt broth supplemented with 0.5% lactalbumin hydrolysate and 500 μg/ml of streptomycin sulphate for 48 hours under anaerobic conditions. A portion of a Mitis Salivarius agar plate (containing 0.001% potassium tellurite) was then streaked with the swabs, incubated for 1 week, then examined for the presence of *S. mutans*.

After swabbing, treatment was begun by injecting 50 μl of a 0.3% Methocel ® suspension of the test compound or Methocel ® (negative control) into each of 4 quadrants in the mouth. Treatment was repeated twice daily except on weekends and holidays, when the animals were treated once daily. This gave a total dose of 200 μl per treatment.

After twenty-eight consecutive days of treatment, the hamsters were sacrificed by guillotine. The skin was removed from the heads and the heads stained for 15 seconds in a 1.0% aqueous solution of Erythrosine-B followed by a running water rinse for 30 seconds. The heads were then randomly presented to the scorer with only a code number for identification. Using a dissecting scope, the buccal and lingual surfaces of each molar were examined for the approximate percentage of the surface covered with plaque.

After all data had been recorded, the codes were broken, the data re-grouped and the various treatment groups compared by a non-parametric one-way analysis of variance.

TABLE 2

Summary of Statistical Data from Plaque Inhibition in the Hamster

| Test | Treatment | Molar Surface Covered with Plaque[a] |
|---|---|---|
| 1 | Methocel ® (control) | 15.51 ± 2.57 |
| | Dodecyl thiouronium phenylphosphonate | 8.82 ± 1.59[b] |
| 2 | Methocel ® (control) | 13.96 ± 1.49 |
| | Tridecyl thiouronium phenylphosphonate | 7.06 ± 1.16[c] |

[a]Refers to the mean scoring value of the relative amount of plaque observed by the scorer on the hamster teeth. Therefore, numbers smaller than control refer to a decrease in the amount of plaque on the molar surface relative to control.
[b]Significantly different from Methocel ® control at $p \leq 0.05$.
[c]Significantly different from Methocel ® control at $p \leq 0.01$.

Other thiouronium phosphonates within the scope of this invention have similar dental prophylactic properties. Since the thiouronium chlorides and bromides of the prior art have offensive odors, unlike the phosphonates used in this invention, as noted earlier, they are rejected by a substantial proportion of test animals. No examples of animal rejection were observed for the phosphonates utilized in this invention.

What is claimed is:

1. A method for treating the teeth and gums of animals which comprises applying to the dental surfaces an effective amount of a compound corresponding to the formula

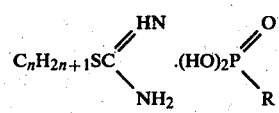

in which n is an integer of from about 10 to about 14, and R is hydrogen, methyl or phenyl.

2. The method of claim 1 wherein n is 12.

3. The method of claim 1 wherein R is phenyl.

4. The method of claim 1 wherein n is 12 and R is phenyl.

5. The method of claim 1 wherein n is 13, and R is phenyl.

6. A composition for treating the teeth and gums of animals which comprises an effective amount of a compound corresponding to the formula

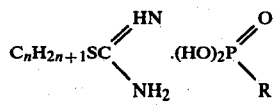

in which n is an integer of from about 10 to about 14 and R is hydrogen, methyl or phenyl in combination with a pharmaceutically acceptable toothpaste, toothpowder, or mouthwash carrier.

7. A composition as claimed in claim 6 wherein the active compound constitutes from about 0.1 to about 0.5 percent of the composition.

8. A composition as claimed in claim 6 wherein the active compound constitutes from about 0.1 to about 0.5 percent and the balance of the composition is a toothpaste, tooth powder or mouthwash.

9. A composition as claimed in claim 6 wherein the active compound is dodecyl thiouronium phenyl phosphonate in an amount of from about 0.1 to about 0.5 percent and the balance of the composition is a toothpaste, tooth powder or mouthwash.

* * * * *